United States Patent [19]
Buckholtz

[11] Patent Number: 5,147,186
[45] Date of Patent: Sep. 15, 1992

[54] BLOOD PUMP DRIVE SYSTEM

[75] Inventor: Dwight A. Buckholtz, Eden Prairie, Minn.

[73] Assignee: Bio Medicus, Inc., Minneapolis, Minn.

[21] Appl. No.: 638,366

[22] Filed: Jan. 4, 1991

Related U.S. Application Data

[62] Division of Ser. No. 389,634, Aug. 4, 1989, Pat. No. 5,021,048.

[51] Int. Cl.$^5$ .................. F16C 1/02; A61M 1/10
[52] U.S. Cl. .................. 417/420; 417/360; 464/29; 415/900; 604/151
[58] Field of Search .............. 417/360, 420, 423.15; 415/140, 900; 464/29, 180, 181; 192/84 PM; 310/103, 104; 604/4, 151; 128/DIG. 12

[56] References Cited

U.S. PATENT DOCUMENTS

| Re. 28,742 | 3/1976 | Rafferty et al. | 415/90 |
|---|---|---|---|
| 413,684 | 10/1889 | Sargent | 415/177.2 |
| 3,085,407 | 1/1964 | Tomlinson | 464/29 |
| 3,089,514 | 5/1963 | Sudmeier | 417/420 |
| 3,169,486 | 2/1965 | Freed | 415/131 |
| 3,194,165 | 7/1965 | Sorlin | 417/353 |
| 3,221,389 | 12/1965 | Cowell | 464/29 |
| 3,228,344 | 1/1966 | Cooper | 416/177 |
| 3,314,512 | 7/1967 | Kerestury | 464/29 |
| 3,368,743 | 2/1968 | Chaboseau | 464/180 |
| 3,411,450 | 11/1968 | Clifton | 417/420 |
| 3,470,824 | 10/1969 | O'Connor | 417/240 |
| 3,487,784 | 1/1970 | Rafferty et al. | 415/71 |
| 3,500,754 | 3/1970 | Boes | 464/180 |
| 3,608,088 | 9/1971 | Dorman et al. | 128/899 |
| 3,638,455 | 2/1972 | Francois | 464/181 |
| 3,647,324 | 3/1972 | Rafferty et al. | 417/423 |
| 3,864,055 | 2/1975 | Kletschka et al. | 415/1 |
| 3,890,969 | 6/1975 | Fischel | 128/146.3 |
| 3,957,389 | 5/1976 | Rafferty et al. | 415/1 |
| 3,970,408 | 7/1976 | Rafferty et al. | 415/60 |
| 4,065,234 | 12/1977 | Yoshiyuki | 417/420 |
| 4,135,253 | 1/1979 | Reich et al. | 415/112 |
| 4,304,532 | 12/1981 | McCoy | 417/420 |
| 4,643,641 | 2/1987 | Clausen et al. | 417/170 A |
| 4,678,409 | 7/1987 | Kurokawa | 417/420 |
| 4,722,661 | 2/1988 | Mizuno | 415/131 |
| 4,895,557 | 1/1990 | Moise et al. | 600/16 |

Primary Examiner—Richard A. Bertsch
Assistant Examiner—Peter Korytnyk
Attorney, Agent, or Firm—Merchant, Gould, Smith, Edell, Welter & Schmidt

[57] ABSTRACT

Perfusion pump driver apparatus for coupling motive power from a controller console to the rotator of perfusion pump. The coupler has a console adapter to connect the coupler apparatus to the pump control console. A pump receptacle is provided in the coupler to connect the pump to the driver. A power transfer mechanism consisting of a bushing and flexible shaft is provided in the coupler to adapt the control console characteristics to the pump characteristics.

1 Claim, 8 Drawing Sheets

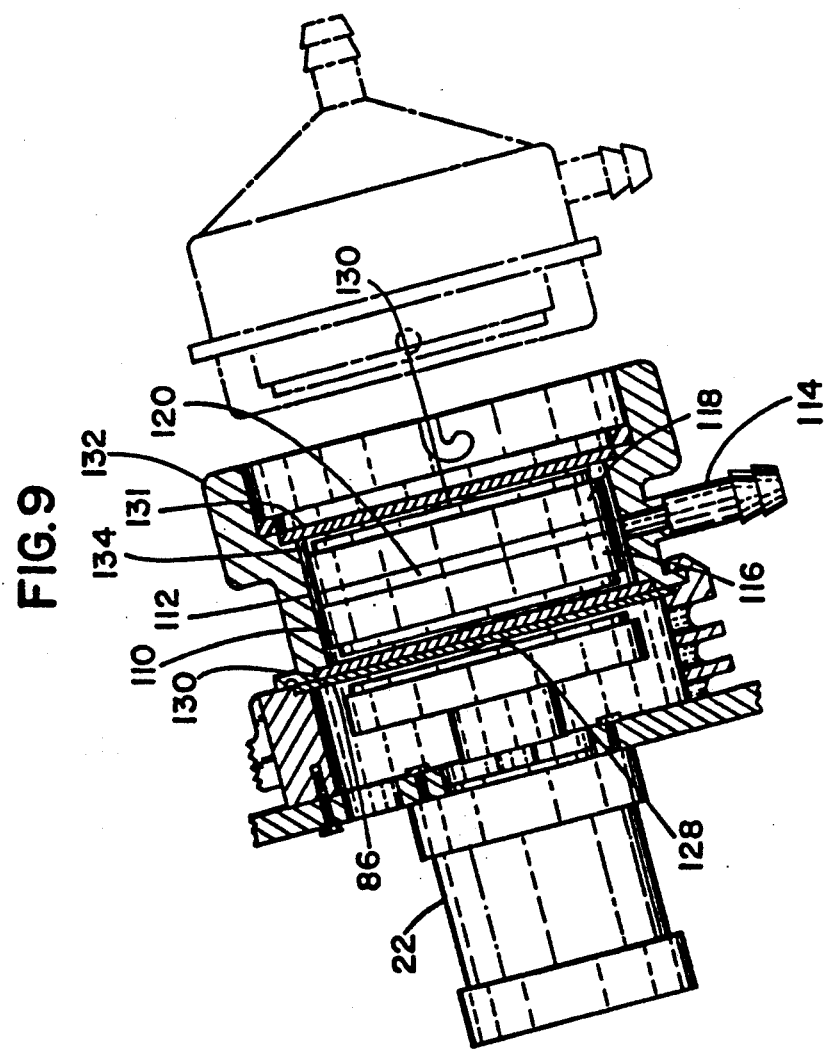

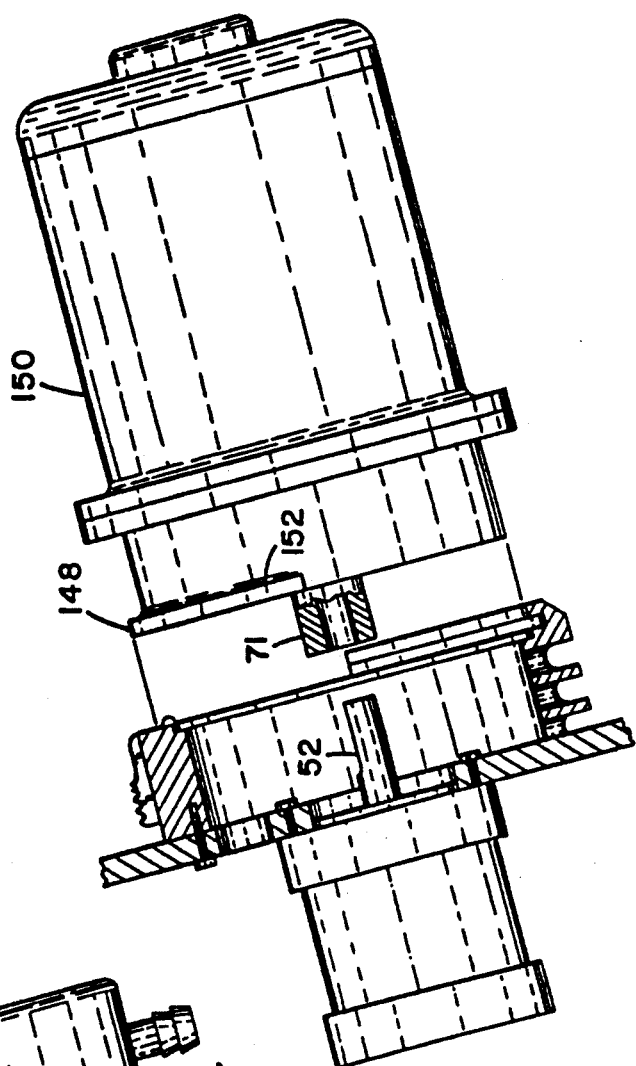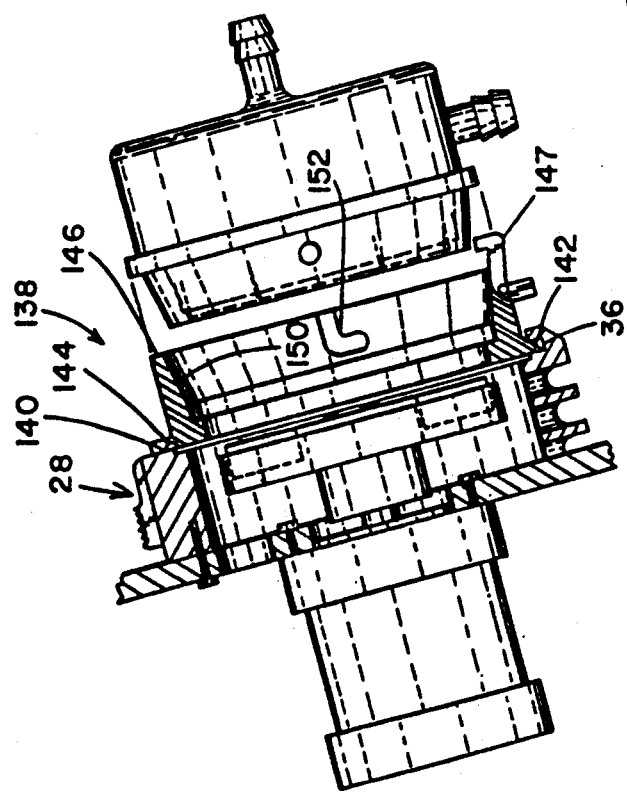

BLOOD PUMP DRIVE SYSTEM

This is a division of application Ser. No. 07/389,634, filed Aug. 4, 1989, now U.S. Pat. No. 5,021,048.

BACKGROUND OF THE INVENTION

This invention relates to blood perfusion pumps. A coupler for connecting a kinetic pump to a perfusion control console is described.

Blood is a fragile material which must be handled carefully. Early efforts at pumping blood in support of surgical procedures involved the use of the peristaltic or roller pump. This type of pump is easy to manufacture from biocompatible materials. This type of pump is also easy to control with simple motor controllers. However, these and other positive displacement pumps are inadequate when used to support some surgical procedures. The principal drawbacks of such pumps are the generation of air emboli, the disruption of tubing connectors and the fracture of pump tubing.

In response to these defects in the prior art, a new type of pump was introduced. U.S. Pat. No. 3,647,324 to Rafferty, E. et al. describes this new type of rotary pump. This type of pump has no vanes or impellers and is now commonly called a kinetic pump. The kinetic pump provides a smooth surface rotator which moves blood from a central inlet to the periphery of a pump housing. Although the angular velocity of the blood within the pump is essentially constant, the linear velocity continues to increase as the radial distance from the inlet increases. To preserve the flow pattern through the pump, the rotators converge so that rotator passages remain constant in cross sectional area. The spacing between the rotator passages varies as an inverse function of the radial distance from the rotator axis. This geometry of the kinetic pump results in the principal benefits of such pumps which are the prevention of cavitation, and the prevention of over pressurization of the blood.

The earliest versions of these pumps were powered by internal motor structures as shown in U.S. Pat. No. 4,037,984 to Rafferty, E. et al. An alterative to the internal motor is taught by U.S. Pat. No. 3,864,055 to Kletschka, which shows a drive shaft protruding from the pump housing.

The problems presented by each of these prior art approaches were overcome by the adoption of the driver apparatus shown in FIGS. 1, 2 and 3. Briefly, the pump is a disposable item which is discarded after a single use. As such, the pump is supplied as a sterilized and sealed unit. The pump is driven by the magnetic coupling of rotating drive magnets located in the control console and driven magnets embedded in the pump rotator.

Although the kinetic pump in its various forms has been successful in a wide variety of clinical settings, sophisticated control apparatus is required to monitor and supervise its operation. Currently, the control apparatus is supplied in a console which houses the drive motor and the supervisory electronics. The modern console may further include RPM monitor and control apparatus, along with pressure and flow monitoring apparatus.

The pump is mounted directly on the console in view of the physician or remotely from the drive console at or near the patient. By locating the pump close to the patient the amount of tubing required to hook the kinetic pump into the patients vascular system is reduced. In either location, the pump is driven magnetically. Typically the pump is placed into a pump receiver located on either, the console or on a remote driver unit.

Each manufacturer has a specialized pump design which renders certain combinations of pumps and consoles incompatible. This strategy prevents the use of incompatible systems and therefore provides additional protection to the patients.

SUMMARY OF THE INVENTION

Couplers in accordance with the present invention, adapt the pump control console to a variety of otherwise incompatible pumps. To accomplish this objective, power transmission structures are incorporated into the coupler. These structures match the power transmission requirements of the pump with the consoles output. Depending upon the pump, the coupler may include gear trains or other speed transformation structures to adapt the rotational speed and direction of the console to the pump.

BRIEF DESCRIPTION OF THE DRAWINGS

In the drawings, like reference numerals indicate corresponding structure throughout the several views in which.

FIG. 9 is a cross section view of an illustrative embodiment of the invention;

FIG. 10 is a cross section view of an illustrative embodiment of the invention;

FIG. 11 is a cross section view of an illustrative embodiment of the invention;

DETAILED DESCRIPTION OF THE PREFERRED EMBODIMENTS

Figure 1:
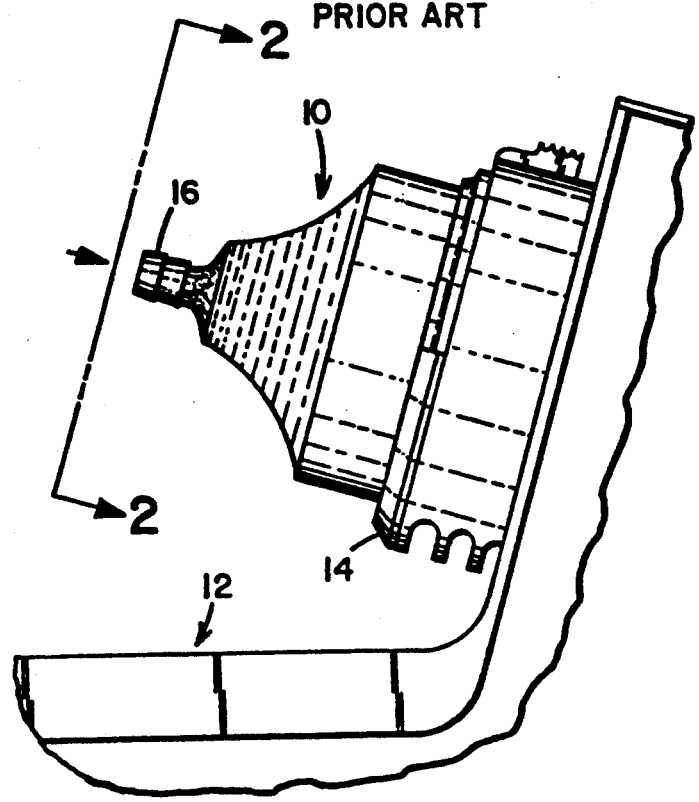
FIG. 1 is a side view of a pump mounted on a console.
Figure 2:
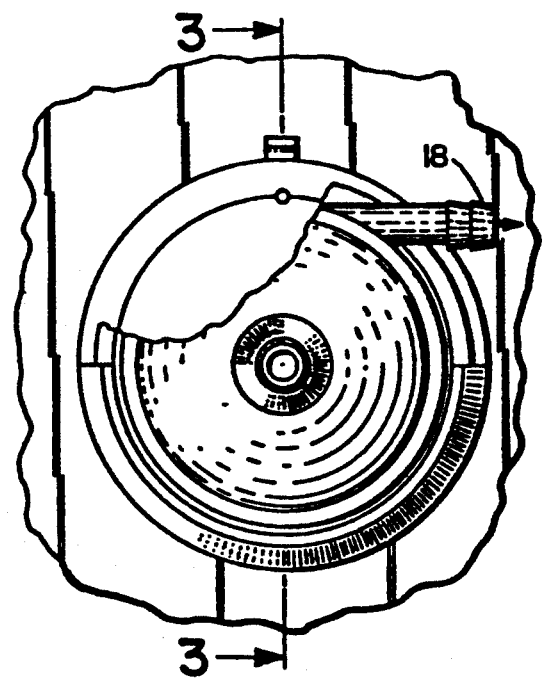
FIG. 2 is a front view of a pump.

FIG. 1, shows a prior art kinetic pump 10 attached to a prior art pump control console 12. The console has a receiver 14 which connects the console 12 with the pump 10. In operation, the tubing coupler 16 located on the pump 10 connects the pump to the patients arterial cannula to receive input blood flow. The output blood flows from the tubing coupler 18 shown on FIG. 2 to the patient cannula. The two figures taken together show the generally circular form of the pump 10.

Figure 3:
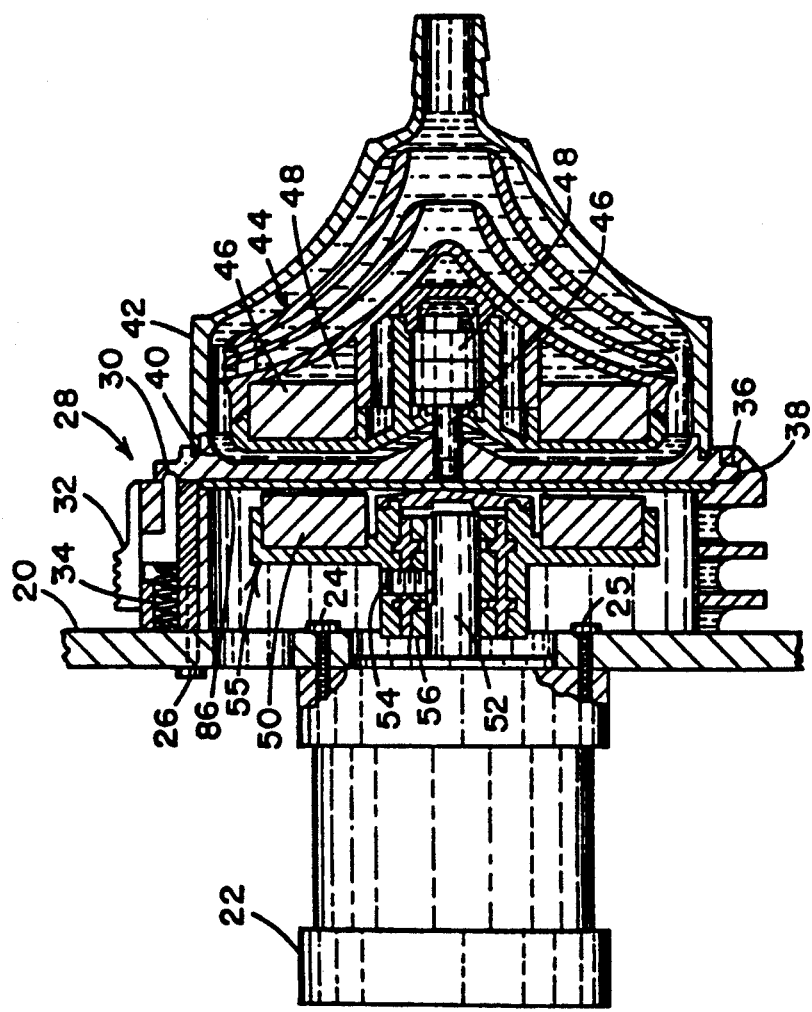
FIG. 3 is a cross section view of a pump mounted on a console.

FIG. 3 shows a cross-section of the receiver 14, the pump 10, and a portion of the console 12. The console wall 20 provides a mounting surface for the pump motor 22. The pump is attached through the use of a plurality of screws shown in the figure as 24 and 25. The receiver 14 is connected to this wall 20 through the use of screws shown in the figure at 26.

The receiver 14 has a detent fixture shown at 28, which engages the pump 10 to retain the pump in the receiver. The detent 28 includes a prong 30 coupled to a thumb slide 32. These elements engage with the pump 10 through the action of the spring 34. The detent structure cooperates with a slot or convolution at the periphery of the backing plate in the receiver 14 to retain the pump flange 38.

The pump 10 has a mounting flange 38 formed in the backing plate 40. The backing plate joins to the pump housing 42. Within the vessel formed by the backing plate and housing there is a rotator assembly shown as 44. The rotator is free to revolve around an axis defined by the shaft 49. This shaft 49 is rigidly attached to the backing plate 40. Sealed cartridge bearing 48 couple the rotator 44 to the shaft 49. Drive magnets 46 positioned within a chamber 11 formed by the backing plate 40 and the rotator 44. This form of construction provides a pump interior which is smooth and biocompatible, for safe handling of the blood.

The motor 22 provides motive power to the pump 10. The preferred form of coupling power represented by this prior art structure. As shown in the figure, driving magnets 50 located near the driven magnets 46 to transmit torque, to the rotator.

As shown in FIG. 3 the pump motor shaft 52 has a flat formed on it to receive a setscrew 54. The setscrew connects the drive-hub 56 to the driving magnets 50.

Figure 4:
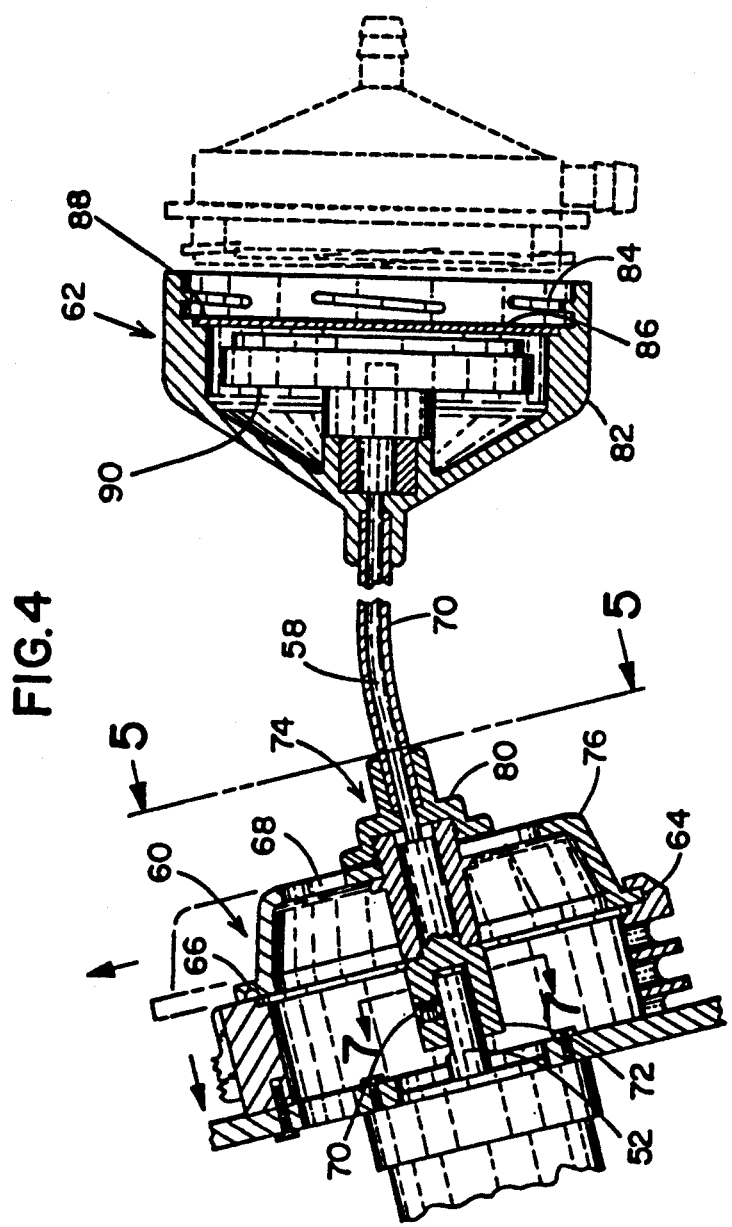
FIG. 4 is a cross section of an illustrative embodiment of the invention.
Figure 5:
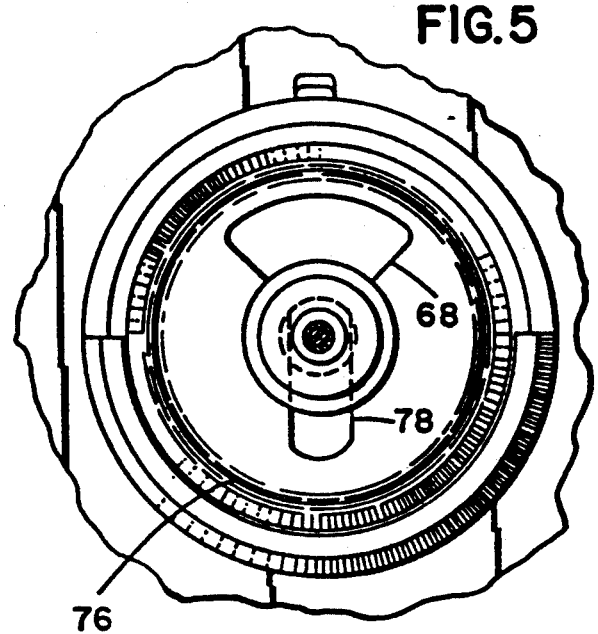
FIG. 5 is a front view of the console adaptor housing of FIG. 4 in the mounted position.
Figure 6:
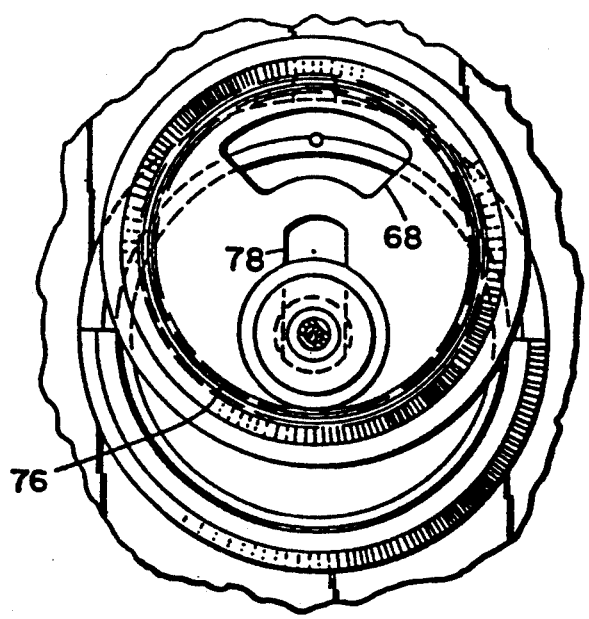
FIG. 6 is a front view of the console adaptor housing of FIG. 4 in the unmounted position.

FIG. 4 shows a coupler constructed in accordance with the teaching of the present invention. The coupler provides for the remote placement of the pump near the patient. The pump however is controlled by the console. To achieve this objective a flexible shaft 58 is used to connect the console to the pump. This coupler has a pump adaptor designated 62 and has a console adaptor designated as 60. This coupler provides for 1:1 power transmission from the console mounted pump motor 22 to the rotator 44.

The console adaptor 60 provides a flange 64 to mate with the annular recess 36 located in the console receiver 14. The flange has recessed groove 66 which engages the prong 30 of the detent 28. A recess 68 provided in the console adapter permits access to the setscrew 70. A collar 72 engages the motor shaft 52 of the pump motor 22 to transmit power to the flexible shaft 58. A flexible sheath 70 surrounds the shaft 58. A bushing designated 74 provides connection between the flexible shaft 58 and the sheath 70 to the pump adaptor 60. Preferably the bushing is mounted in a longitudinal slot 78 formed in the console adaptor housing 76.

To use this coupler the operator first slides the collar 72 onto the motor shaft 52. Next, the annular flange 64 of the console adaptor housing is positioned into the recess 36. During this operation the detent 28 will engage the recessed groove 66. Next, the operator will tighten the setscrew 70 to secure the collar 72 to the shaft 52. Once this operation has been completed the operator may tighten the bushing retaining nut 80.

Figure 7A:
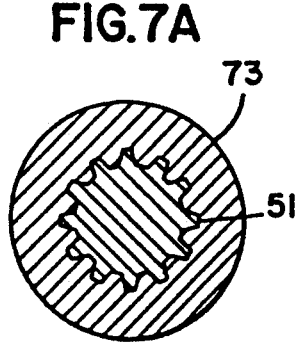
FIG. 7 and 7A are a cross sections of a motor drive shaft assemblies for the illustrative embodiment of FIG. 4.
Figure 7:
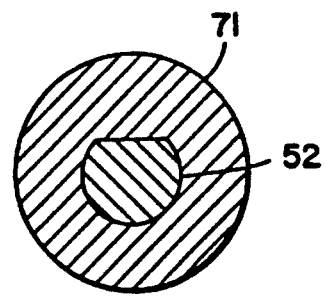

Alternate forms of mechanical connection between the motor and the collar may be employed without departing from the scope of this invention. In FIGS. 7 and 7a two examples of alternate structure are shown. In FIG. 7 a broached collar mates with motor shaft without the use of a set screw. Similarly a broached spline collar 73 is used with a splined motor shaft 51.

Figure 8:
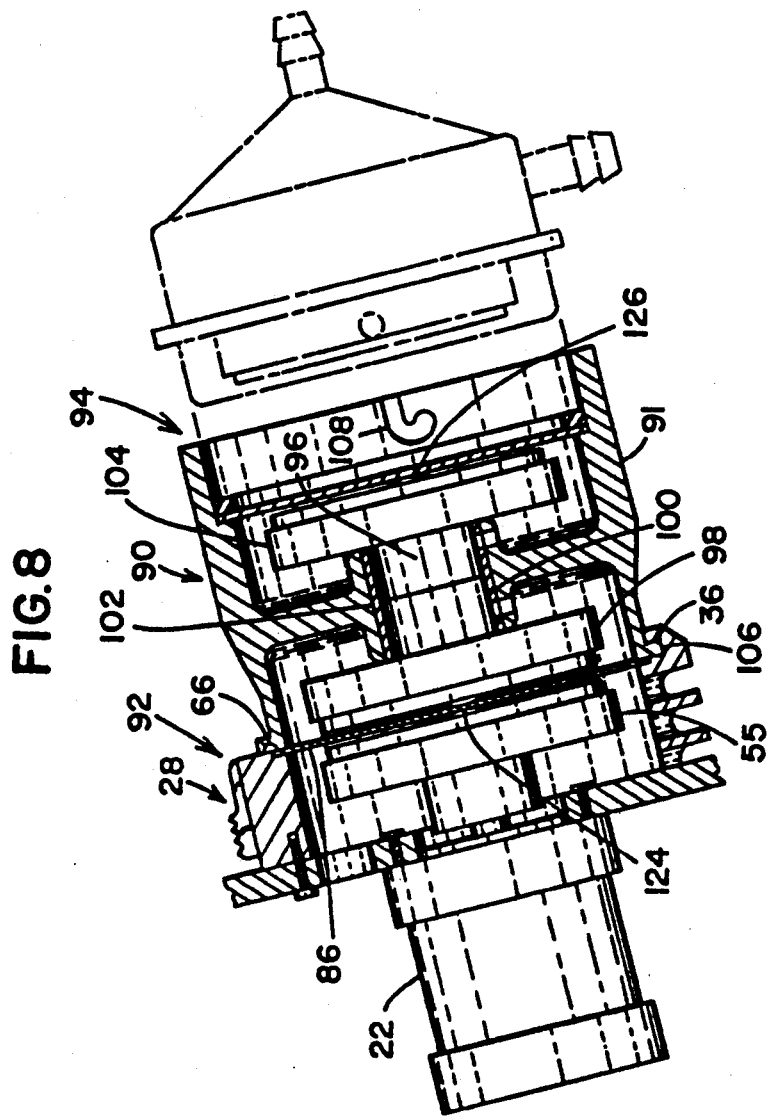
FIG. 8 is a cross section view of an illustrative embodiment of the invention.

The kinetic pump shown in phantom view in FIG. 4 mounts to the pump receptacle 82 through the use of a helical fitting. This is shown by helical threads 84 formed in the receptacle. It should be appreciated that other forms of mounting are contemplated within the scope of this invention. For example, FIG. 8 shows a bayonet type of pump fitting which will be discussed in connection with that drawing. The pump receptacle housing 82 contains a thin nonferrous cover 86 mounted within an annular recess 88 to separate the remote drive plate 90 from the pump backing plate.

FIG. 8 shows a coupler 93, having a console adaptor 92 and a pump receptacle 94. In this embodiment of the invention the magnetic driver 55 remains unchanged. However, an intermediate power transfer assembly 96 connects the drive motor 22 to the kinetic pump. A magnetic driver 55 placed close to a complimentary drive receiver 98. The drive receiver 98 mounted on a shaft 100 which rides in a bushing 102. A cooperating magnetic driver 104 mounted on the shaft 100 to transmit power to a kinetic pump located in the pump receptacle 94. The housing 91 includes a flange 106 to mate with the annular recess 36 located in the console receiver 14. The flange has recessed groove 66 which engages the prong of the detent 28. This is a highly desirable form of coupling because it requires no modification of the console itself. Additionally the coupler may be inserted into the console as though it were a pump, which is a familiar operating room procedure. The pump receptacle portion of the coupler receives the cylindrical base of a kinetic pump. This base member is retained through the use of a bayonet fitting which includes a slot 108 which is fabricated in the housing 91.

Magnet to magnet adaption is required when the console and pump have differing pole pieces which prevent the reliable transfer of power.

One drawback with the system shown in FIG. 8 is introduction of an additional bearing surface in the power transmission system. It is undesirable to add components where they do not offer an improved operational result.

FIG. 9 shows an alternate form of magnet to magnet adaptor. In contrast to the system of FIG. 8 there is no bearing support shaft. The magnet assembly 110 located in the housing 112 floats on a hydrodynamic bearing surfaces 118 and 116. These bearing surfaces maintain the position of the magnet assembly 110 in the cavity. A fluid fitting 114 is provided to fill the cavity with a lubricating fluid to operate the hydrodynamic bearings. It is contemplated that the magnet assembly will be formed from first 116 and second 118 pole pieces. If the number of magnetic domains differs between the pole pieces, a magnetic permeable barrier 120 should be placed between them. The purpose of the barrier is to shunt the magnetic fields so that the two pole pieces do not interfere with each other. Good torque transfer between a driving magnet and a driven magnet requires matching pole pieces. In this embodiment the console motor 22 connects with a magnetic driver 55. The driver is placed in close proximity to the first pole piece. This arrangement results in good torque transfer from the console to the coupler. The number of magnetic domains on the second pole piece is selected to match the number used in the compatible pump.

In the embodiments shown in FIGS. 8 and 9 the end-play of the pole pieces is controlled by thrust buttons 124 and 126. Thrust button 124 cooperates with cover 86 in the embodiment shown in FIG. 8. FIG. 9 shows an embodiment were the thrust button 128 abuts with a first coupler cover 130. Similarly, the thrust button 130 abut with a second coupler cover 131. The coupler covers and the housing 132 define the magnet chamber 134.

FIG. 10 shows a coupler 138 which includes a console adaptor 140 comprising an annular flange 142 for engaging the console recess 36. The flange 142 has a circumferential groove 144 to accept the console mounted detent 28. The pump receptacle 146 has a conical surface 150 to align the kinetic pump with the drive magnets 50. The pump may be held or secured through the use of a pin lock structure comprising a pump mounted pin and a lock groove 152 which has a generally horizontal retention surface, or by a spring loaded clamping device 147 which captures its flangs.

Figure 12:
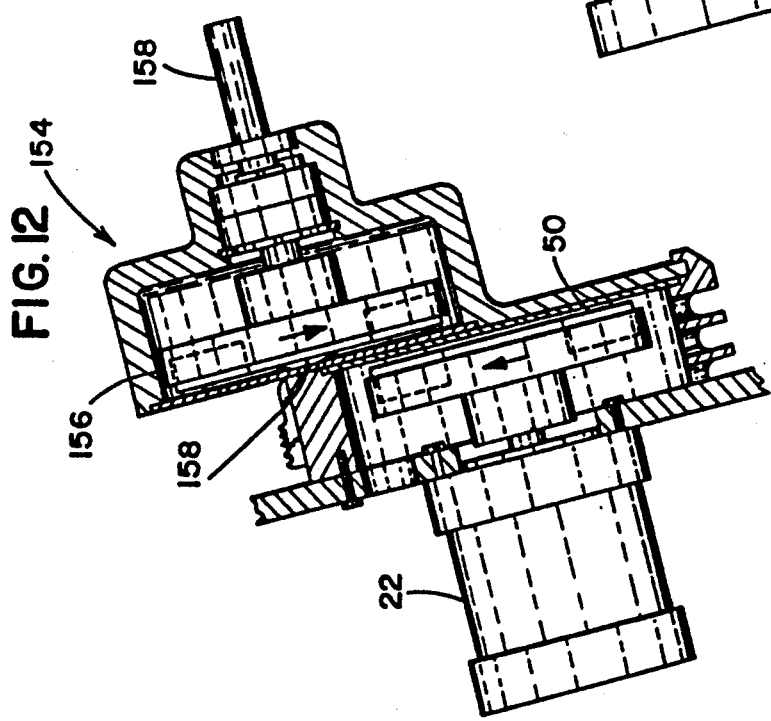
FIG. 12 is a cross section view of an illustrative embodiment of the invention.

FIG. 12 shows a coupler 154 which has structure to reverse direction of rotation. The coupler includes driven magnets 156 in an eccentric position to reverse the direction of rotation of the output shaft. The driven magnets are located in close proximity to the driving magnets 50. The driving magnets 50 are connected to the console motor 22 as described in connection with earlier figures. Axial end play of the driven magnets 156 is controlled with a thrust button 158 located on the driven magnets. The axis of rotation of the driven magnets is displaced from the axis of rotation of the console motor. This displacement causes the direction of rotation to be reversed. It should be appreciated that the output shaft 158 may be used to drive a flexible shaft as shown in FIG. 4 or may alternatively be used to drive a shaft driven pump as shown in FIG. 11.

FIG. 11 shows an adapter 148 which spaces a shaft driven pump 150 from the console. The coupler 148 has a flange 152 which may be rotated into engagement with the recess 36. The pump shaft 71 may be inserted onto the console motor shaft 52 and the pump maybe rotated into the receiver to secure it to the console.

Figure 13:
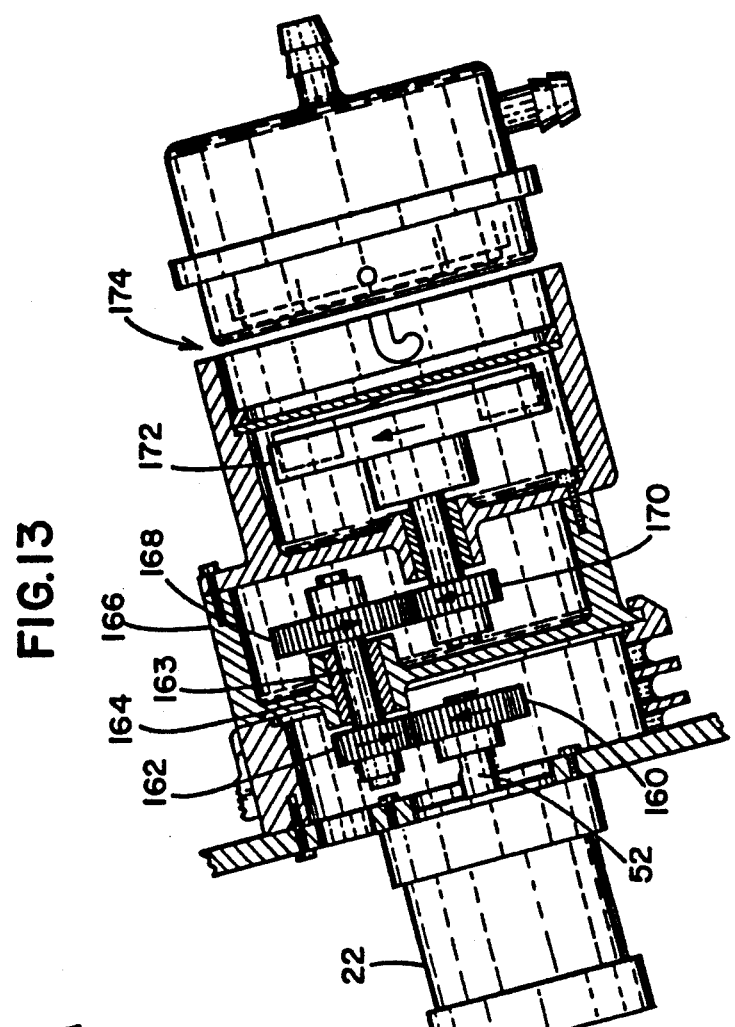
FIG. 13 is a cross section view of an illustrative embodiment of the invention.

FIG. 13 shows a coupler which includes a gear train power transfer mechanism. This gear train may be used to either increase or decrease the speed of rotation. This form of coupler is useful to match the console speed range with the requirements of the pump. The conventional pump control console offers variable speed motor control over a wide range. However, some types of kinetic pumps operate at nominal speeds which do not overlap with the motor speeds available from the console. It should also be understood that gear trains of the type disclosed may be used to reverse the direction of rotation as taught by FIG. 12. The use of gears for the power transfer mechanism is preferred if the pump has significant torque requirements. In the embodiment shown in FIG. 13 a first gear 160 is mounted on the motor shaft 52. This gear transfers power to a second gear 162 located on an intermediary shaft 163. The shaft is journaled in a bushing 164. The bushing is attached to the housing 166. A secondary gear train which includes a third 168 and fourth 170 gear couple power to the magnet pole piece 172. The driving pole piece 172 is concentric with the pump receptacle. The gear ratios selected would depend on the requirements of the kinetic pump being driven. The selection of kinetic pumps is not restricted to the type shown since other pumps having vanes in the combination with smooth converging rotators may be used with out departing from the spirit and scope of the invention.

What is claimed is:

1. Apparatus for pumping blood, comprising:
   a pump controller console having a motor and having a pump receiver; said pump receiver including detent means for securing flanges and an annular recess for retaining flanges;
   kinetic pump means for imparting kinetic energy to said blood; said pump means including rotator means for increasing the angular velocity of said blood; drive magnet means embedded in said rotator means adapted for coupling energy to said rotator;
   coupler means for interconnecting said kinetic pump to said console; said coupler means including a pump receptacle and a console adapter, the console adapter comprising an annular housing 76 having, a peripheral flange 64 to mate with said annular recess on said console pump receiver 14 and having a recessed slot 66 to engage said detent on said console pump receiver; power transfer means having a bushing 74 for coupling to a flexible shaft 58 located in said annular housing 76 and having coupling means 72 for connection to said motor.

* * * * *